(12) United States Patent
Buetikofer et al.

(10) Patent No.: US 7,377,908 B2
(45) Date of Patent: May 27, 2008

(54) INSERTION DEVICE FOR INSERTING AN INJECTION NEEDLE

(75) Inventors: Markus Buetikofer, Muensingen (CH); Simon Scheurer, Bern (CH); Martin Wyss, Konolfingen (CH)

(73) Assignee: Disetronic Licensing AG, Burgdorf (CH)

( * ) Notice: Subject to any disclaimer, the term of this patent is extended or adjusted under 35 U.S.C. 154(b) by 70 days.

(21) Appl. No.: 11/329,403

(22) Filed: Jan. 10, 2006

(65) Prior Publication Data
US 2006/0173414 A1 Aug. 3, 2006

Related U.S. Application Data

(63) Continuation of application No. PCT/EP2004/008156, filed on Jul. 21, 2004.

(30) Foreign Application Priority Data
Jul. 21, 2003 (DE) ................. 103 33 118

(51) Int. Cl.
*A61M 5/178* (2006.01)
(52) U.S. Cl. .................. 604/164.01
(58) Field of Classification Search ........ 604/158–163, 604/164.01, 192, 198, 263, 110, 181, 187, 604/272, 93.01, 264, 268, 523, 288–289; 128/919
See application file for complete search history.

(56) References Cited

U.S. PATENT DOCUMENTS 4,755,173 A * 7/1988 Konopka et al. ...... 604/167.02
4,950,252 A 8/1990 Luther et al.
5,176,662 A * 1/1993 Bartholomew et al. ..... 604/513
5,522,803 A * 6/1996 Teissen-Simony .......... 604/177
5,533,974 A 7/1996 Gaba
5,562,629 A * 10/1996 Haughton et al. .......... 604/158
6,090,068 A 7/2000 Chanut
6,355,021 B1 * 3/2002 Nielsen et al. .............. 604/263

FOREIGN PATENT DOCUMENTS

| EP | 0 734 739 A2 | 10/1996 |
| EP | 0 747 084 A2 | 12/1996 |
| FR | 2 725 902 | 10/1994 |

* cited by examiner

*Primary Examiner*—Manuel Mendez
(74) *Attorney, Agent, or Firm*—David E. Bruhn; Dorsey & Whitney LLP (57) ABSTRACT

An insertion device for inserting an injection needle into a tissue including a needle holder carrying the injection needle and a protection device for covering the injection needle after the removal thereof from the tissue wherein the needle holder is mounted to move along the needle axis in relation to the protection device and for insertion of the injection needle the needle holder and protection device are moved more closely together and wherein at least one catch is provided on at least one of the needle holder and protection device, which firmly engages the needle holder with the protection device in an extended relative position. The invention encompasses a catheter head having a base body, a flexible cannula extending from the base body and the insertion device with the protection device.

14 Claims, 6 Drawing Sheets

INSERTION DEVICE FOR INSERTING AN INJECTION NEEDLE

CROSS-REFERENCE TO RELATED APPLICATION(S)

This application is a continuation of International Patent Application No. PCT/EP2004/008156, filed on Jul. 21, 2004, which claims priority to German Application No. 103 33 118.2, filed on Jul. 21, 2003, the entire contents of both of which are incorporated herein by reference.

BACKGROUND

The invention relates to devices for inserting a needle or the like into tissue, and to methods of making and using such devices. More particularly, it relates to an insertion device for inserting an injection needle into a tissue, more particularly wherein the insertion device is part of a catheter head, and, more particularly, wherein the catheter head is part of an infusion set.

Many different types of insertion devices for inserting an injection needle into a tissue are known in the prior art. In addition to having a needle holder from which the injection needle protrudes, more recent insertion devices also comprise a protection device for protecting and/or covering the injection needle after withdrawal from the tissue. The protection device serves to protect the person using the insertion device from needle-stick injuries, as the injection needle is freely accessible after withdrawal from the tissue. Such insertion devices are used in various medical or therapeutic devices and procedures in which an active fluid substance or another liquid has to be introduced into a body tissue.

Insertion devices have been used for catheter heads for, for example, infusion sets. The catheter head serves as port for introducing a liquid active substance, e.g., insulin, growth hormones. etc., into the body tissue. For this purpose, the catheter head is applied for a considerable length of time on the surface of the body tissue. A flexible cannula protrudes from an underside of the catheter head into the body tissue. Because of its flexibility, the cannula can follow the movements and changes of the body tissue and thus causes as little discomfort as possible for the person using the catheter head. Above the tissue surface, a catheter leads from the catheter head to a receptacle containing the liquid active substance. The catheter is in fluidic communication with the cannula. For introducing the flexible cannula into the body tissue, a rigid injection needle can be used which, for example, is guided through the cannula such that the latter bears firmly on the injection needle, and whose insertion tip protrudes beyond the cannula. After the cannula has been introduced into the tissue, the rigid injection needle is pulled from the cannula, said cannula remaining in the tissue. The injection needle accordingly forms an insertion aid for the flexible cannula.

An insertion device with an injection needle as insertion aid for a catheter head as described above is described in WO 00/03757. The insertion device has a housing from which an injection needle protrudes in such a way that it reaches through a base body of the catheter head and extends through the flexible cannula of the catheter head. Arranged on one side of the housing of the insertion device, there is a protection device in the form of a sleeve cap which is pivotable relative to the housing and which is open at one end in the direction of the needle. In a first state for insertion of the injection needle, the sleeve cap protrudes from the housing perpendicularly with respect to the needle axis. After insertion of the injection needle, or flexible cannula, the insertion device is detached from the base body of the catheter head, the injection needle being withdrawn from the tissue or the flexible cannula. After the withdrawal of the insertion device, the sleeve cap can then be pivoted relative to the housing and over the injection needle. In doing this, the injection needle is bent sideways in the pivoting direction of the sleeve cap and is partially surrounded by the latter. On that side of the housing opposite from the sleeve cap, catch devices are provided in which the sleeve cap engages after pivoting, in such a way that it is not pivoted back by the restoring force of the bent needle. However, after withdrawal from the tissue or from the base body of the catheter head, the injection needle is initially exposed, as a result of which there is a risk of injury to the user. Moreover, the sleeve cap has to be guided manually over the injection needle, as a result of which there is an additional risk of injury because various maneuvers have to be performed in the vicinity of the injection needle.

SUMMARY

It is an object of the present invention to make available an insertion device, for inserting an injection needle into a tissue, whereby risk of injury after removal of the injection needle from a tissue is reduced or eliminated, whereby a protection device for protecting or covering the injection needle can be easily arranged around the injection needle, whereby the injection needle is at all times protected during withdrawal, and for which no additional maneuvers are required in order to protect the injection needle after removal of the insertion device.

It is a further object of the invention to make available a catheter head for medical or pharmaceutical applications, whereby risk of injury from using an injection needle as insertion aid for a flexible cannula is reduced or eliminated, an insertion aid can be easily detached after introduction of the flexible cannula, and the catheter head can be easily placed on a tissue.

Accordingly, in one embodiment, the present invention comprises an insertion device for inserting an needle into tissue, comprising a needle holder carrying the needle, a protector for covering the needle after removal from the tissue, wherein the needle holder is axially movable relative to the protector and for insertion of the needle is generally inside the protector, and a catch for holding the needle holder and protector together in a position in which the needle holder is generally outside the protector.

In one embodiment, the present invention comprises an insertion device for inserting an injection needle into a tissue comprising a needle holder carrying the injection needle and a protection device for covering the injection needle after the removal thereof from the tissue, wherein the needle holder is mounted to move axially in relation to the protection device and for insertion of the injection needle the needle holder and protection device are moved more closely together, and wherein at least one catch is provided on at least one of the needle holder and protection device, the at least one catch engaging the needle holder with the protection device in an extended relative position. The invention encompasses a catheter head having a base body, a flexible cannula extending from the base body and the insertion device with the protection device.

In one embodiment, the present invention comprises an insertion device for inserting an injection needle into a tissue, comprising a needle holder from which the injection needle protrudes and a protection device for protecting the injection needle after removal from the tissue, wherein the needle holder is mounted so as to slide along the needle axis in relation to the protection device and, for insertion of the injection needle, the needle holder is in a position in which it is pushed together with the protection device, at least one catch device provided on at least one of the needle holder and the protection device, which catch device firmly locks the needle holder and the protection device together at least in a position in which they are drawn apart from one another.

In one embodiment, according to the present invention an insertion device for inserting an injection needle into a tissue comprises a needle holder from which the injection needle protrudes, and a protection device for protecting the injection needle on removal from the tissue. The needle holder is mounted so as to slide along the needle axis in relation to the protection device. For this purpose, the needle holder and the protection device can be designed like sleeves so that they can be pushed one into the other. The needle holder can be pushed over the outside of the protection device or can be pushed into the inside of the protection device. For insertion of the injection needle, the needle holder is in a position in which it is pushed together with the protection device. The injection needle protrudes from the protection device such that it can be inserted into the tissue. In this position, access to the injection needle can be prevented by a protective cap, which is removed shortly before the insertion. When needle holder and protection device are being drawn apart, the needle holder is moved relative to the protection device along the needle axis into a drawn-out position in which the tip of the injection needle is surrounded by the protection device in some preferred embodiments, the protection device remains fixed relative to the tissue. The injection needle is pulled out of the tissue directly into the inside of the protection device and is at no time exposed. In order to lock the needle holder and the protection device securely to one another at least in the drawn-out position, at least one catch device is provided on the needle holder and/or the protection device. In this way, after it has been locked, the needle holder cannot fall back into a pushed-together position in which the injection needle could protrude from the protection device. In this regard, it is advantageous if, when needle holder and protection device are drawn apart, the at least one catch device not only blocks them against renewed sliding together in the completely drawn-out position, but also blocks them against sliding together even after just partial drawing apart, when a part of the injection needle still lies inside the tissue.

According to a further aspect of the present invention, an insertion device according to the invention forms a part of a catheter head for medical and pharmaceutical applications, as is disclosed, for example, in the application DE 102 55 817.5 belonging to the owner of the present application. Such a catheter head has a base body with a flexible cannula protruding from it. The insertion device is used for introducing the flexible cannula into a tissue. The insertion device is in this case designed in the manner described above.

In a preferred embodiment of the present invention, the protection device of the insertion device is connected to the base body of the catheter head, the base body resting on a surface of the tissue. It is conceivable in principle to connect the protection device to the base body in a detachable manner. However, this is not necessary in the described embodiment. In the position in which needle holder and protection device are pushed together, the injection needle protrudes through the base body. In some embodiments, the injection needle preferably protrudes from the base body perpendicularly with respect to a surface of the base body via which it rests on the tissue surface. For introducing the flexible cannula of the catheter head, the injection needle extends through the flexible cannula and its tip protrudes beyond the latter. After insertion of the injection needle or flexible cannula into the tissue, the needle holder is moved relative to the protection device along the needle axis and, in this process, the injection needle is pulled out of the tissue or cannula. In the position in which the needle holder has been drawn out, the injection needle is pulled back completely into the protection device.

If it is desired that the insertion device be provided detachably on the catheter head, the insertion device may be arranged on the catheter head in such a way that the insertion device, in the drawn-out position of the needle holder, can be pulled out from the base body in a direction perpendicular to the needle axis, i.e. parallel to a surface of the tissue. In this way it is possible to avoid a situation where, by removing the insertion device from the catheter head, the catheter head is lifted from the tissue surface and the flexible cannula is pulled at least partially from the tissue. However, it is also possible in principle to remove the insertion device from the base body in a direction parallel to the needle axis.

Using an insertion device and a catheter head according to the present invention, it is possible to remove an injection needle from a tissue without risk of injury to the user. During removal from the tissue, and in the withdrawn position, the injection needle is covered and inaccessible. By means of the catch device between needle holder and protection device, it is not possible to expose the injection needle after it has been drawn back into the withdrawn position of the needle holder relative to the protection device. The needle protection is already arranged over or around the injection needle in a simple manner upon withdrawal of the injection needle from the tissue, and no additional operating step is needed in order to arrange the protection device around the injection needle. The insertion device can be detached from the catheter head in a simple manner, without any risk of the catheter head being lifted from the tissue surface. This is because the movement for detaching the insertion device from the catheter head is perpendicular to the movement for withdrawing the injection needle or for withdrawing the needle holder from the protection device.

In a preferred embodiment of the present invention, at least one guide arrangement is provided between protection device and needle holder for the purpose of guiding the needle holder during its movement relative to the protection device along the needle axis. The guide arrangement can be formed, for example, by one or more guide grooves which are provided on the protection device and into which a projection arranged on the needle holder engages. Of course, the guide grooves can also be provided on the needle holder and, accordingly, the projections on the protection device. Other suitable complementary structures or arrangements may be used as well.

For locking the needle holder to the protection device in the drawn-out position of the needle holder, the catch device comprises at least one first limit stop for blocking the needle holder in the direction of drawing apart, and at least one second limit stop for blocking the needle holder in the direction of pushing together. For example, a first limit stop can be formed by a projection on the needle holder striking against an abutment on the protection device when the needle holder is in the drawn-out position. Of course, the projection can also be provided on the protection device, and the abutment on the needle holder. Such an abutment can be formed, for example, by a step or a projection or an outer surface of the needle holder or of the protection device. The second limit stop for blocking against sliding together is preferably arranged on at least one element acting in the manner of a leaf spring. The second limit stop can be provided by a projection on the leaf spring element which strikes against an abutment in the drawn-out position of the needle holder. For the catch device, one or more leaf spring elements can be provided on the needle holder or on the protection device or also on both of these. A leaf spring element is formed, for example, by a slat-like extension on the needle holder or on the protection device, which slat-like extension protrudes, substantially parallel to the needle axis, from the needle holder in the direction of the protection device or from the protection device in the direction of the needle holder. The extension is arranged fixedly on the needle holder or on the protection device. It is preferably made in one piece with the needle holder or the protection device, for example by injection molding. However, the extension is able to bend relative to the needle holder or the protection device and can thus be pretensioned. In principle, however, the leaf spring element can also be formed by being fixed with opposite ends on the needle holder or protection device.

For an insertion device according to the present invention, it is of course also possible to use catch devices other than leaf spring elements in the form of slat-like extensions with the corresponding limit stops, provided that secure locking is possible in the drawn-out position of needle holder and protection device. For example, catch elements could be used which are pretensioned by helical springs or elastic rubber elements which are compressed when the needle holder and the protection device are drawn apart and which expand in the withdrawn position. As far as the configuration of the catch device is concerned, it must simply be ensured that the catch mechanism is based on the principle of the slidability of the needle holder along the longitudinal axis of the injection needle relative to the protection device, in order to permit locking as a consequence of the needle being withdrawn from the tissue.

In some embodiments, the needle holder and the protection device preferably have a right-parallelepiped shape, with a broad or long side and with a short or narrow side. A first limit stop for blocking against the drawing apart of needle holder and protection device is formed by two slat-like extensions which are each arranged on opposite short sides. The second limit stop for blocking against the sliding together of needle holder and protection device is formed by four slat-like extensions, with two of said extensions on each broad side. A sliding together of needle holder and protection device is thus prevented by four symmetrically arranged points of engagement between needle holder and protection device. In principle, it is possible to provide all the slat-like extensions for the first limit stop and for the second limit stop either on the needle holder or on the protection device. It is also possible, however, to provide the extensions for a first limit stop on the needle holder, and to provide the extensions for a second limit stop on the protection device, or vice versa.

In one embodiment of the catch device, it is possible for the slat-like extensions to be in a pretensioned state when the needle holder and the protection device are in the pushed-together position, and for said extensions to be released into an untensioned blocking state when the needle holder and protection device are in the drawn-apart position. In another embodiment, it is possible for the slat-like extensions to be in an untensioned state in the pushed-in position, and to be pretensioned, for example by a ramp, when needle holder and protection device are drawn apart. It is advantageous if the projections on the slat-like extensions engage in consecutive abutments, for example inside the guide arrangement, and, in this way, a renewed sliding together of needle holder and protection device is prevented even during the drawing-apart movement. Accordingly, the locking of the needle holder to the protection device by means of the catch device can take place, according to the invention, by untensioning of the slat-like extensions or by pretensioning of the slat-like extensions. To block the needle holder relative to the protection device in the drawn-out position, the projections on the slat-like extensions cooperate with the respectively opposite abutments.

Care should be taken to ensure that, during insertion of the injection needle, the needle holder is not moved relative to the protection device simply by the resistance exerted by the tissue in relation to the injection needle. If the slat-like extensions are pretensioned while the needle holder is being drawn out of the protection device, the resistance force of the extensions, which acts counter to the pretensioning, may be sufficient to prevent the needle holder being moved relative to the protection device as a result of the insertion of the injection needle. However, in some embodiments, a locking device can additionally be provided for locking and unlocking the needle holder and protection device in the pushed-together position on the insertion device. In the locked state, the needle holder cannot be moved relative to the protection device and therefore, during insertion of the injection needle into the tissue, also cannot accidentally be pushed out from the protection device. After insertion of the injection needle, the locking device can be unlocked so that the needle holder can be moved relative to the protection device. The locking device can advantageously be connected to two points of engagement for the needle holder, such that the locking device can be unlocked at the same time as the needle holder is being drawn out from the protection device. This can be done, for example, by pressing in grip surfaces into the needle holder. Moreover, the locking device can also be coupled to the catch device. For this purpose, for example, corresponding projections can be provided on the slat-like extensions, said projections striking against an abutment in the pushed-together position and being released from these abutments by the pressure on the grip surfaces of the needle holder.

DETAILED DESCRIPTION OF THE DRAWINGS

With regard to fastening, mounting, attaching or connecting the components of embodiments of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems. Any suitable electronic, electrical, communication, control or controller, computer or processing components may be used, including any suitable electrical components and circuitry, wires, wireless components, sensors, chips, boards, micro-processing or control system components, software, firmware, hardware, etc. References positional orientation (e.g., upward and downward) are used herein for ease of description.

Figure 1:
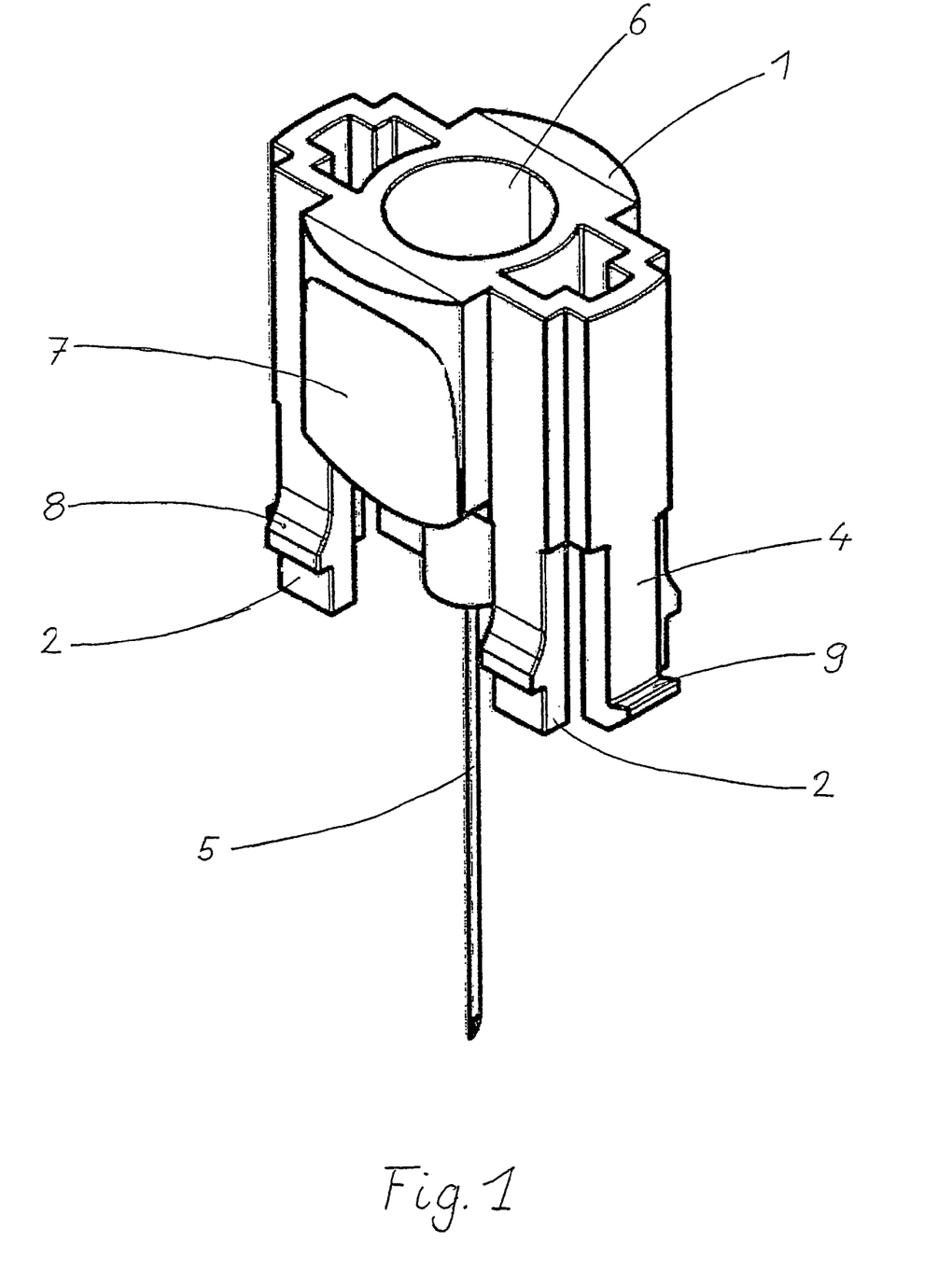
FIG. 1 is a perspective view of a needle holder of an insertion device of one embodiment of the present invention.

FIG. 1 shows a needle holder 1 of an insertion device according to one embodiment of the present invention, in which the needle holder 1 is mounted slidably inside a protection or covering device (not shown in FIG. 1). An injection needle 5 projects downward from the needle holder 1 in the direction of a tissue. The needle holder 1 has substantially the shape of a right parallelepiped with two broad sides, from which slat-like extensions 2 extend parallel to the injection needle 5, and two short sides, from which in each case one slat-like extension 4 extends parallel to the needle 5. The extensions 2 and 4 form one complementary part of a catch device of the insertion device according to the invention. In its inside, the needle holder 1 has a cylinder-like opening 6 in which further devices, for example a needle introducer device, can be accommodated. However, the needle holder 1 can also be closed on the top face. Arranged on each of the broad sides of the right-parallelepiped needle holder 1, there is a grip surface 7 on which the needle holder 1 can be grasped and guided from two opposite sides.

The extensions 2 of the broad side of the needle holder 1 protrude from the needle holder 1 in such a way that they can bend to a certain extent, i.e., at least a portion of their length can move out beyond the plane formed by the broad side of the needle holder. In this embodiment, the extension 4 protrudes from the short side of the needle holder 1 in a rigid manner. However, it is also possible in principle for the extension 4 to be made so that it is flexible and/or can bend, i.e. it or a portion of it can be moved out beyond the plane formed by the short side of the needle holder 1. As a result of the bending property of the extensions 2 and, if appropriate, also of the extensions 4, these extensions can be pretensioned. They accordingly may be thought of and/or referred to as spring elements, leaf spring element, etc.

Arranged in the lower area of the slat-like extensions 2, i.e. adjacent to the free end or in an area lying remote from the rest of the needle holder body, there are outwardly directed steps 8 which have a downwardly directed surface oriented perpendicular to the needle axis. Arranged on a lower area near the free end of the extensions 4, there is a projection 9 which points outward in relation to the needle holder 1 and is provided with an upwardly directed surface oriented perpendicular to the needle axis.

Figure 2:
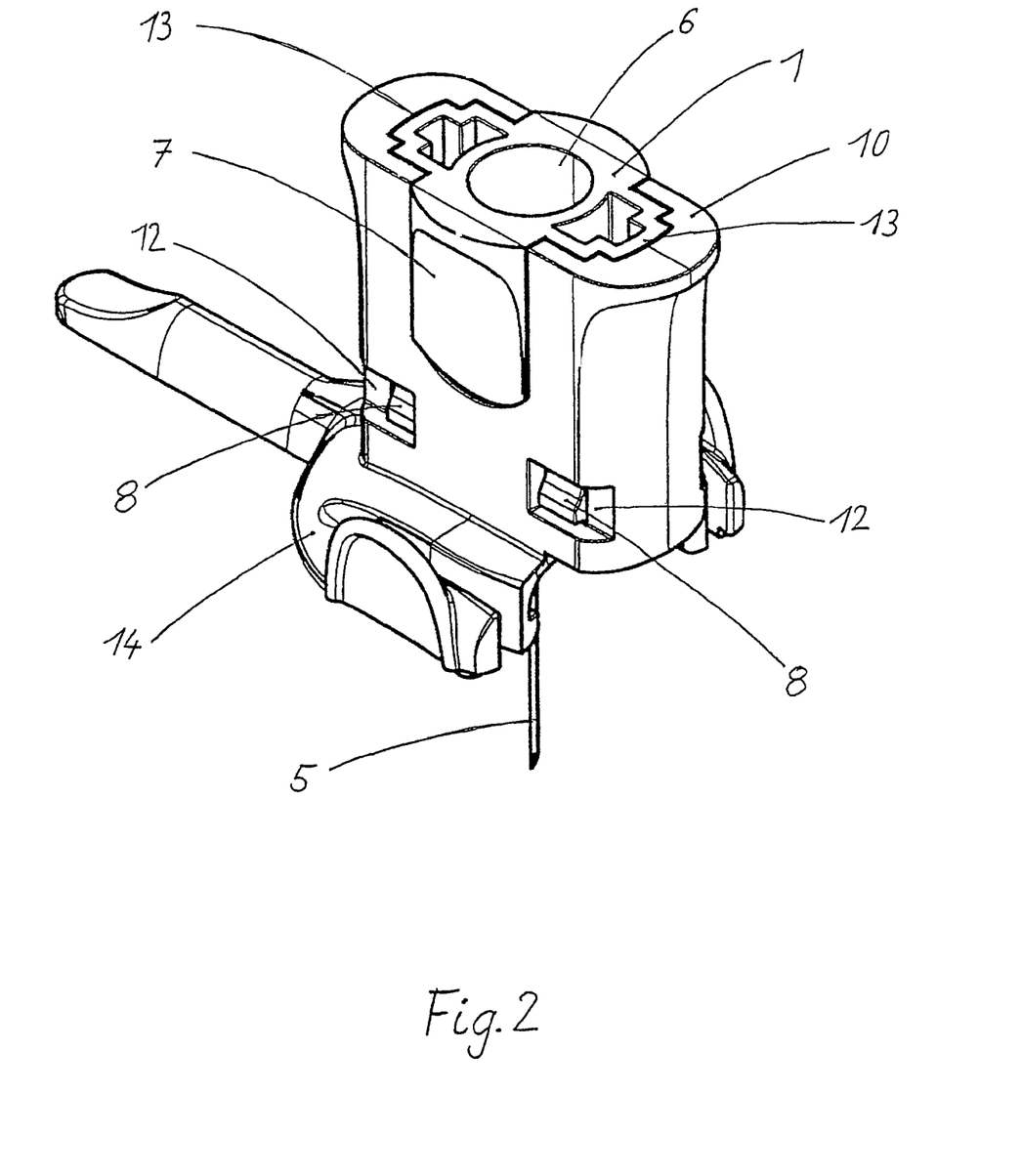
FIG. 2 is a perspective view of an insertion device with a needle holder according to FIG. 1 in a position in which needle holder and protection device have been pushed together.

In FIG. 2, the needle holder 1 from FIG. 1 is shown in a position in which it has been pushed into a protection device 10. The protection device 10 is arranged on a base body 14, as can be fitted for example onto a catheter head, the injection needle 5 protruding or extending downward through the base body 14. The protection device 10 has a right-parallelepiped shape similar to the needle holder 1 and, in its inside, it has a cavity complementing or matching the needle holder 1. On a broad side of the wall of the protection device 10, there is a recess into which a grip surface 7 can be introduced with a form fit.

In a lower area of the broad side of the protection device 10, the wall of said protection device 10 is provided with openings 12 in which the steps 8 of the slat-like extensions 2 of the needle holder 1 engage when the needle holder is in the pushed-in position. In this position, the slat-like extensions 2 are in an untensioned state or in a state with only slight pretensioning, in which state the extensions 2 are bent inward.

On the short side of the right-parallelepiped protection device 10, on its inside surface, said protection device 10 has guide grooves 13 which each extend parallel to the needle axis. The slat-like extensions 4 of the needle holder 1 run at least partially inside the guide grooves 13. The projections 9 of the extensions 4 at any rate project into the guide grooves 13 in the inside of the protection device 10.

With the steps 8 protruding through the openings 12, a locking mechanism is obtained by which a sliding of the needle holder 1 relative to the protection device 10 is made difficult. To be able to slide the needle holder 1 relative to the protection device 10, it is necessary to overcome a high initial resistance created by bevels which are arranged on the steps 8 and which adjoin an edge of the openings 12 in the wall of the protection device 10. The protection device 10 is connected securely to the base body 14 in the direction of the needle axis. To withdraw the needle holder 1 from the protection device 10, the high initial resistance has to be overcome, the bevels on the steps 8 being guided along the edges of the openings 12 of the protection device 10 in such a way that the slat-like extensions 2 are bent inward and pretensioned until the outside of the steps 8 comes to lie on the inside of the wall of the protection device. To withdraw the needle holder 1 from the protection device 10, it is then necessary to overcome the frictional force between the steps 8 and the inside of the protection device 10. However, it is also possible to release the steps 8 from engagement in the openings 12 by pressing in the grip surfaces 7 so that the extensions 2 are bent slightly inward. When the needle holder 1 is released, the extensions 2 move back out again.

Figure 3:
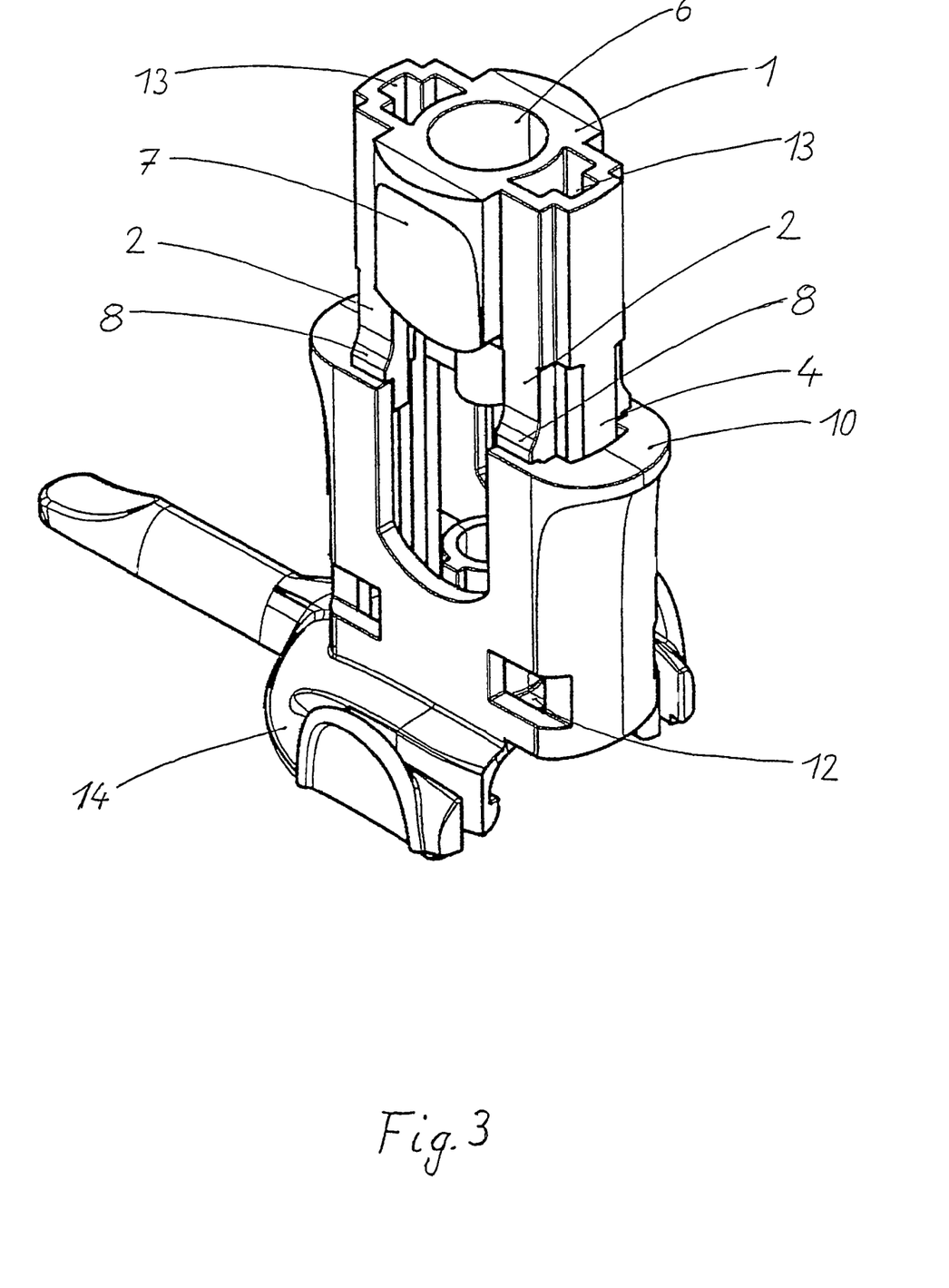
FIG. 3 is a perspective view of an insertion device according to FIG. 2 in a position in which it has been drawn apart.

FIG. 3 shows the insertion device according to one embodiment with a needle holder 1 drawn out from the protection device 10. To slide the needle holder 1 from the pushed-in position (generally inside the protector) to the drawn-out position (generally outside the protector), the needle holder 1 is held via the grip surfaces 7 and pulled upward out of the protection device 10 counter to the direction of insertion of the injection needle 5. The needle holder 1 is drawn out from the protection device 10 until the projections 9 on the extensions 4 abut the wall of the top face of the protection device 10 which delimits the guide grooves 13. At the same time as the projections 9 abut the wall of the protection device 10, the steps 8 on the extensions 2 emerge from the top face of the protection device 10, i.e. above the top wall of the protection device. Because of their pretensioning, the extensions 2 move outward, and the downwardly directed surface of the steps 8 comes to lie opposite the upper wall of the protection device 10. In this position, the needle holder is in a position in which it has been drawn out relative to the protection device 10.

On the inner face of its broad side, the protection device 10 can have catches, for example in the form of steps or depressions, which come to lie opposite the steps 8 of the extensions 2 during the drawing out of the needle holder 1.

As the needle holder 1 is drawn out from the protection device 10, the steps 8 on the extensions 2 can, by virtue of their pretensioning, engage in the depressions or catch above the steps in such a way that the needle holder 1, also when being drawn out from the protection device 10, is blocked by these catches against sliding back into the protection device 10.

In the first embodiment shown, the slat-like extensions 2 and the steps 8 form, together with the outside face of the upper wall of the protection device 10 acting as abutment for the steps 8, a first limit stop which blocks against the needle holder 1 being pushed into or pushed back into the protection device 10. The extensions 4 and the projections 9 form, together with the inside face of the upper wall of the protection device 10 or the boundary of the guide grooves 13 acting as abutment for the projections 9, a second limit stop which blocks the needle holder 1 against being drawn farther out from the protection device 10. In this position, the needle holder 1 is locked securely to the protection device 10, and the injection needle 5 is substantially completely surrounded circumferentially by the protection device 10. In this position, the insertion device can be removed from the tissue surface and be disposed of without risk of injury from the injection needle.

Figure 4:
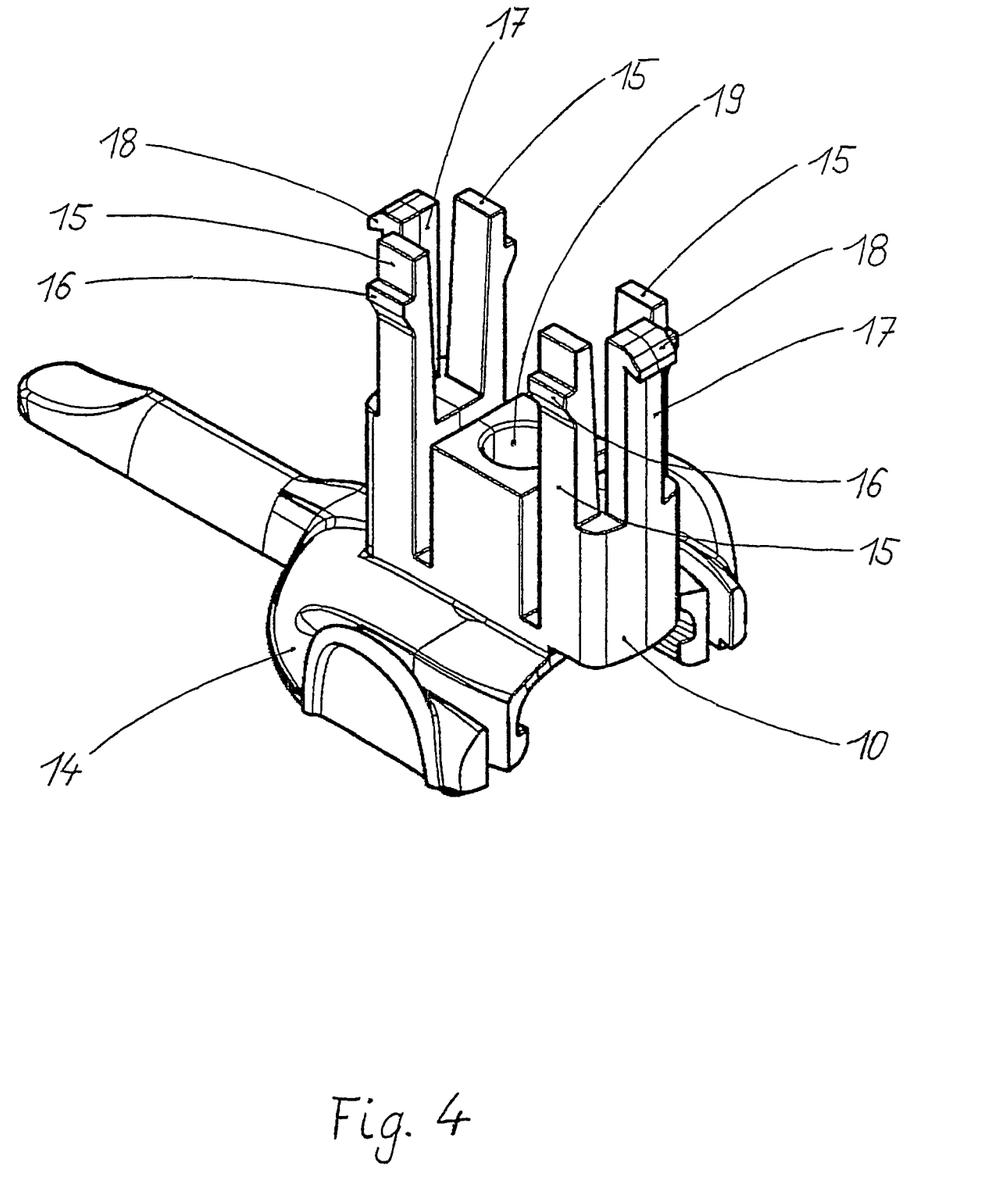
FIG. 4 is a perspective view of a protection device of another embodiment of the present invention.

FIG. 4 shows a protection device 10 according to another embodiment of an insertion device according to the present invention, in which the protection device 10 comes to lie inside the needle holder 1. The protection device 10 is a right parallelepiped, with a broad side and a short side. Provided on the broad side, there are two slat-like extensions 15 which are substantially parallel to the surface of the broad side and project upward, i.e. in a direction away from a tissue. Corresponding extensions 15 are formed on the opposite broad side. Arranged in an upper area on the extensions 15, there is a step 16 which has an upwardly directed surface oriented perpendicular to the needle axis and which points outward. Formed on the short side, there is a slat-like extension 17 which is substantially parallel to the surface of the short side and like the extensions 15 projects upward from the protection device 10. On the opposite short side of the protection device 10 there is a corresponding extension 17. At the end of the extensions 17, there is a projection 18 which points outward from the protection device 10 and has a downwardly directed surface oriented perpendicular to the needle axis. The extensions 15 and 17 protrude from the protection device 10 in a bendable manner, such that they can be pretensioned like leaf springs, in the same way as the extensions 2 and 4 of the first embodiment. The extensions 15 and 17 form, together with the steps 16 and the projections 18, a part of the catch device according to the invention.

An opening 19 is formed in the central area of the protection device 10. An injection needle 5 fitted on the needle holder 1, and projecting perpendicularly downward from the needle holder 1 in the direction of a tissue, is guided through the opening 19 of the protection device 10 and also passes through the base body 14 so that it protrudes downward from the base body 14 and can be inserted into a tissue, through which a needle can be guided such that it can protrude from the underside of the base body 14.

The protection device 10 of the insertion device in FIG. 4 is placed on the top face of a base body 14 which forms part of a catheter head. The base body 14 is placed with its underside onto the surface of a tissue such that the protection device 10 is also fixed relative to the tissue.

Figure 5:
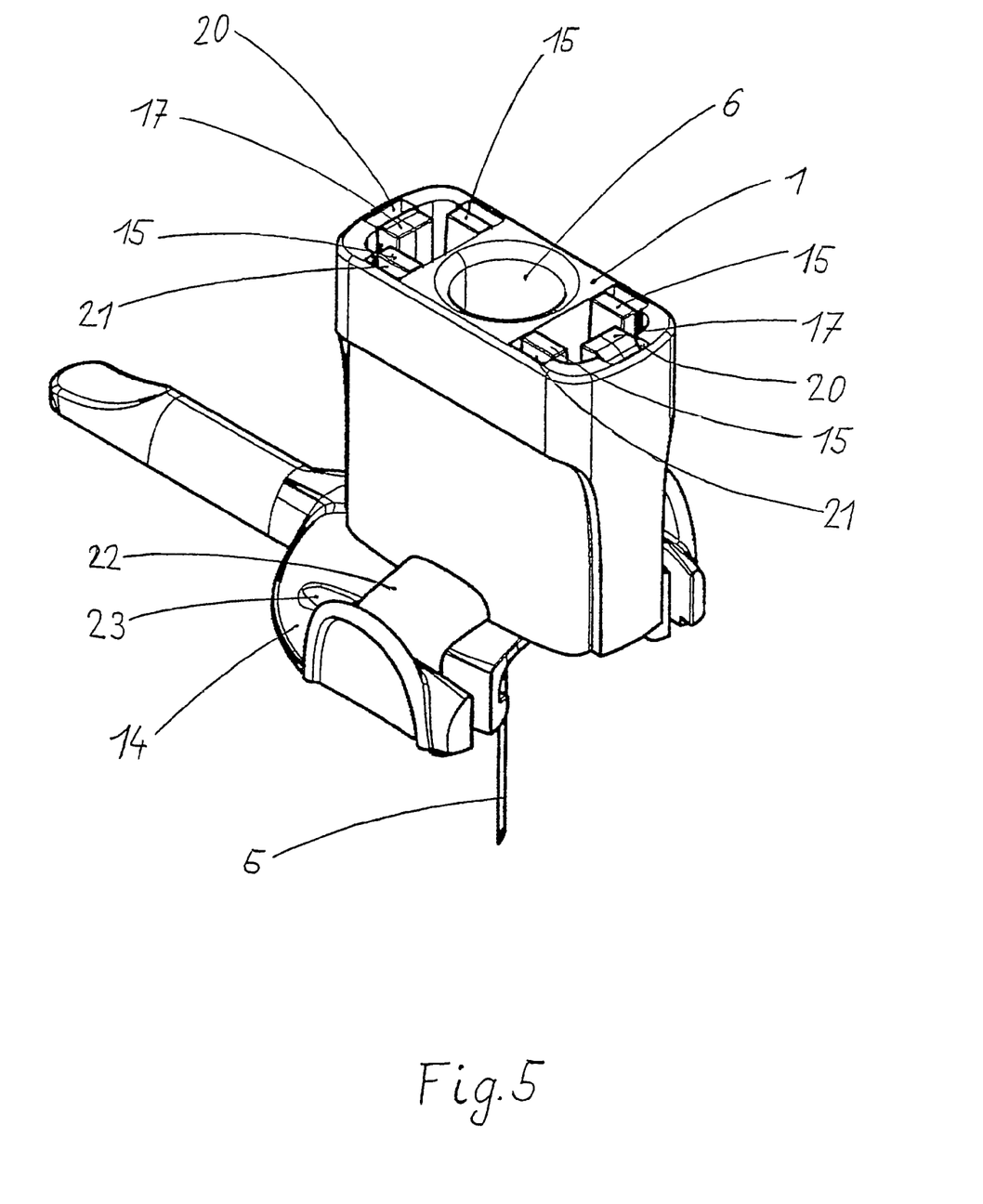
FIG. 5 is a perspective view of an insertion device with a protection device according to FIG. 4 in a position in which needle holder and protection device have been pushed together.

In FIG. 5, a needle holder 1 has been pushed on over the protection device 10. The needle holder 1 is situated in a position in which it has been pushed together with the protection device 10. The needle holder 1 is substantially a right parallelepiped, such that it fits slidably onto the protection device 10. To guide the needle holder 1 on the protection device 10, guide grooves 20 are provided on the inside faces of the needle holder 1 in line with the extensions 17, and also guide grooves 21 in line with the extensions 15. The steps 16 of the extensions 15 or the projections 18 of the extensions 17 engage partially in the guide grooves 20, 21, respectively, or a part of the extensions. When the needle holder and the protection device are drawn apart, the steps 16 and the projections 18 are guided inside the guide grooves such that a simple sliding movement is permitted. The guide grooves 21 for the extensions 15 may have a ramp-like structure in order to pretension the extensions 15 when the needle holder 1 and the protection device 10 are drawn apart. At the lower end, the guide grooves 20 have a border parallel to the underside of the protection device 10, so that, when the needle holder 1 and the protection device 10 are drawn apart, the projection 18 of the extension 17 abuts against this border. The guide grooves 21 for the extensions 15, by contrast, open out at the bottom from the protection device, i.e. they open into the underside of the protection device 10. The steps 16 of the extensions 15 could therefore emerge from the guide grooves 21 in the direction of the underside of the needle holder 1.

At the lower edge of each broad side, the needle holder 1 has wings 22 which protrude perpendicularly from it and are angled downward in their end area. With the angled part, the wings 22 can engage in grooves or recesses 23 of the base body 14 and thus contribute to stabilizing the needle holder 1. It is also possible to use the wings 22, for example, to block a catch mechanism or locking mechanism of the base body 14.

Figure 6:
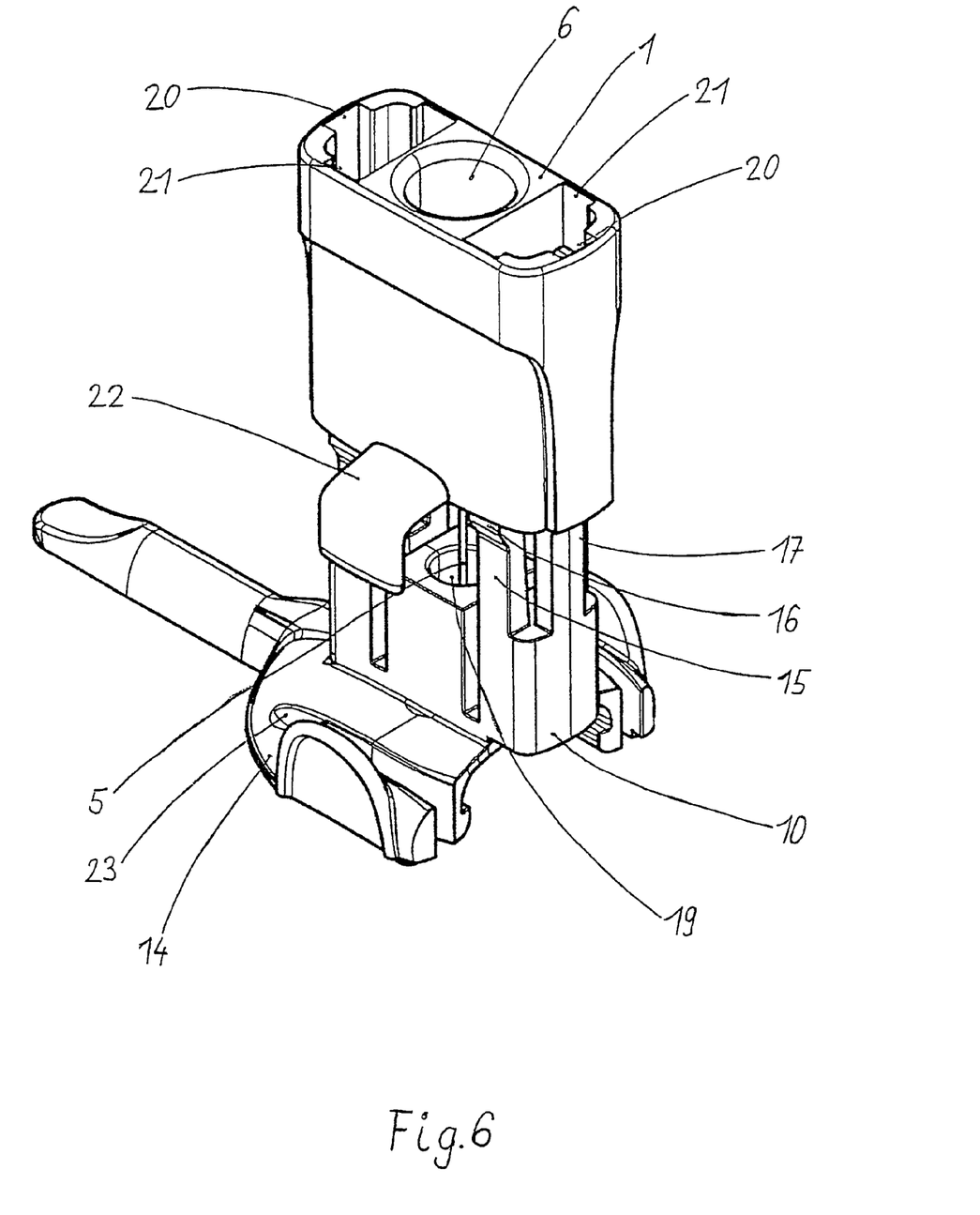
FIG. 6 is a perspective view of an insertion device according to FIG. 5 in a position in which it has been drawn apart.

The insertion device according to the second embodiment is shown in FIG. 6 in a position in which the needle holder 1 and the protection device 10 are drawn apart. The needle holder 1 can be pulled from the protection device 10 until the projections 18 of the extensions 17 abut the border of the guide grooves 20. At the same time, the steps 16 of the extensions 15 emerge from the guide grooves 21 and, as a result of their pretensioning, engage the underside of the needle holder 1, i.e. the bottom edge of the wall on the broad side of the needle holder 1. In this position, the needle holder 1 and the protection device 10 are securely locked to one another, since further pulling of the needle holder 1 is blocked by the extensions 17 abutting against the borders of the guide grooves 20, and renewed pushing-together of the needle holder 1 over the protection device 10 is blocked by the steps 16 of the extensions 15 abutting against the bottom edges of the needle holder 1.

In the drawn out state, the injection needle 5 is drawn back completely into the protection device 10 and is surrounded by it in the circumferentially. Above all, the tip of the injection needle 5 remains inside the opening 19 of the protection device 10, even though central areas of the injection needle are visible. The block in which the opening 19 is provided can, however, have an elongate shape in such a way that all areas of the injection needle are surrounded by it and the injection needle 5 is no longer visible.

As in the first embodiment of the present invention, it is also possible in the second embodiment to provide grooves or steps for the extensions 15 in the guide grooves 21 so that the steps 16, when the needle holder 1 is pulled out from the protection device 10, strike against an opposite groove or step and renewed sliding of the needle holder 1 onto the protection device 10 is blocked. In this way, after insertion of the injection needle and the start of withdrawal of the injection needle from the tissue by pulling the injection holder 1 from the protection device 10, renewed insertion of the injection needle into the tissue is ruled out. If, for example, the injection needle 5 serves as an insertion device in a catheter head, this avoids damage to the flexible cannula by the needle tip.

The present invention has been explained using one illustrative embodiment with slat-like extensions 2 and 4 mounted on the needle holder 1, and using a second illustrative embodiment with slat-like extensions 15 and 16 mounted on the protection device 10. However, it is also possible in principle to provide such extensions both on the needle holder 1 and also on the protection device 10, in which case guide grooves for the extensions can be provided in the respectively complementary part. Moreover, it is also possible to use one and the same extension to block against further withdrawal and to block against a sliding back in the retracted position of needle holder 1 and protection device 10. The number of slat-like extensions can be varied, on condition that a secure locking of the needle holder 1 and the protection device 10 is ensured.

An insertion device according to the present invention can, as described, be used particularly advantageously as an insertion aid for a flexible cannula on a catheter head. However, it is possible in principle for an insertion device according to the invention also to be used in other medical and pharmaceutical applications. In particular, a fluid active substance can also be administered directly through the injection needle. The insertion device according to the present invention may also be used in other fields, including those concerning delivery of substances or the making of connections for the delivery of substances.

Embodiments of the present invention, including preferred embodiments, have been presented for the purpose of illustration and description. They are not intended to be exhaustive or to limit the invention to the precise forms and steps disclosed. Obvious modifications or variations are possible in light of the teachings herein. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

INDEX 1 needle holder
2 extension
4 extension
5 injection needle
6 opening
7 grip surface
8 step
9 projection
10 protection device
12 opening
13 guide groove
14 base body
15 extension
16 step
17 extension
18 projection
19 opening
20 guide groove
21 guide groove
22 wing
23 groove

The invention claimed is:

1. An insertion device for inserting an injection needle into a tissue, comprising:
 a needle holder from which the injection needle protrudes;
 a protection device for protecting the injection needle after removal from the tissue, wherein the needle holder is mounted so as to slide along the needle axis in relation to the protection device, and, for insertion of the injection needle, the needle holder is in a position in which it is pushed together with the protection device,
 at least one catch device being provided on the needle holder and/or the protection device, which catch device firmly locks the needle holder and the protection device together at least in a drawn-apart position, wherein after the needle holder and the protection device have been drawn apart, a pushing back movement of the needle holder relative to the protection device is blocked; and
 wherein the protection device is releasably connected to a base, resting on the tissue, of a catheter head such that the movement to release the insertion device is perpendicular to the movement to remove the injection needle.

2. The insertion device as claimed in claim 1, wherein, when the needle holder and the protection device are drawn apart, the protection device remains fixed relative to the tissue.

3. The insertion device as claimed in claim 2, wherein in an extended position of the needle holder, the injection needle is surrounded in the circumferential direction by the protection device.

4. The insertion device as claimed in claim 3, wherein the device can be withdrawn from the base body in a direction parallel to the tissue surface when the needle holder is in the position in which it has been drawn apart.

5. The insertion device as claimed in claim 1, wherein after the needle holder and protection device have been drawn apart, the catch device blocks against a sliding back of the needle holder relative to the protection device.

6. The insertion device as claimed in claim 1, wherein the catch device comprises at least one first limit stop for blocking the needle holder in the direction of drawing apart, and at least one second limit stop for blocking the needle holder in the direction of pushing together.

7. The insertion device as claimed in claim 6, wherein at least one of the first and second limit stops comprises one or more leaf springs.

8. The insertion device as claimed in claim 6, wherein at least one of the first and second limit stops comprises a projection on a leaf spring.

9. The insertion device as claimed in claim 1, wherein, when the needle holder is in the pushed-together position, a leaf spring is in a pretensioned state, and, when the needle holder is in the drawn apart position, said leaf spring is in an untensioned blocking state.

10. The insertion device as claimed in claim 1, wherein, when needle holder and protection device are drawn apart in the drawn apart position, a leaf spring is brought into a pretensioned state, and, in the retracted position, is in an untensioned blocking state.

11. The insertion device as claimed in claim 1, further comprising a locking device for locking and unlocking the needle holder in the pushed-together position.

12. A catheter head for medical and pharmaceutical applications, comprising a base body, a flexible cannula protruding from the base body, and an insertion device for introducing the flexible cannula into a tissue, the insertion device comprising:

a needle holder from which the injection needle protrudes, a protection device for protecting the injection needle after removal from the tissue, and at least one catch device being provided on one of the needle holder and the protection device, which catch firmly locks the needle holder and the protection device together at least in a drawn-apart position in which they are drawn apart from one another; and wherein after the needle holder and the protection device have been drawn apart, a pushing back movement of the needle holder relative to the protection device is blocked; and wherein the protection device is releasably connected to a base, resting on the tissue, of the catheter head such that the movement to release the insertion device is perpendicular to the movement to remove the injection needle.

13. The catheter head as claimed in claim 12, wherein the injection needle comprises an insertion aid for the flexible cannula.

14. The catheter head as claimed in claim 13, whereby the insertion device is detachably connected to the catheter head.

* * * * *